United States Patent [19]
Bozman

[11] Patent Number: 5,759,028
[45] Date of Patent: Jun. 2, 1998

[54] ORTHODONTIC BONDING SYSTEM

[75] Inventor: John F. Bozman, Bradenton, Fla.

[73] Assignee: GAC International, Inc., Central Islip, N.Y.

[21] Appl. No.: 694,377

[22] Filed: Aug. 8, 1996

[51] Int. Cl.$^6$ .................................................. A61C 7/00
[52] U.S. Cl. .................... 433/9; 433/24; 206/369
[58] Field of Search ........................ 433/8, 9, 24, 229, 433/136, 43; 206/369, 776, 778, 460

[56] References Cited

U.S. PATENT DOCUMENTS

| | | | |
|---|---|---|---|
| 4,204,325 | 5/1980 | Kaelble | 433/9 |
| 5,015,180 | 5/1991 | Randklev | 433/9 |
| 5,328,363 | 7/1994 | Chester et al. | 433/9 |
| 5,354,199 | 10/1994 | Jacobs et al. | 433/9 |
| 5,542,844 | 8/1996 | Perret, Jr. | 433/9 |

*Primary Examiner*—Cary E. O'Connor
*Attorney, Agent, or Firm*—Kenyon & Kenyon

[57] ABSTRACT

A bracket container is provided for storing a plurality of orthodontic brackets having bases coated with a light curable adhesive. The container includes a housing and a tray slidably mounted in the housing. The tray includes an upper surface having a plurality of recesses, each for receiving one of the brackets. The tray is movable between a closed position in which the housing covers the recesses in the tray and an open position in which at least some of the recesses are not covered by the housing. The housing comprises substantially opaque material to limit exposure of the brackets to light when the tray is in the closed position. A method of bonding orthodontic brackets to a patient's teeth is also provided. In accordance with the method, a set of orthodontic brackets suitable for bonding on the patient's teeth is first selected. Then, a light curable cement is applied on a rear bonding surface of the base of each bracket to prepare the bracket for bonding at a predetermined later time. Each bracket is then placed in a tray that is inserted into a container housing to significantly limit exposure of the brackets to light. Next, the teeth of the patient are prepared for bonding. Each bracket is then retrieved from the container tray and placed on the tooth on which it is to be bonded. A curing light is then applied on the brackets to cure the cement on each bracket to bond the bracket on the tooth.

7 Claims, 2 Drawing Sheets

ORTHODONTIC BONDING SYSTEM

TECHNICAL FIELD OF THE INVENTION

The present invention relates generally to orthodontic brackets and, more particularly, to methods and apparatus for bonding such brackets to patients' teeth.

BACKGROUND OF THE INVENTION

Orthodontic appliances such as orthodontic brackets are used in orthodontic treatment for applying corrective forces to misaligned teeth. Orthodontic brackets are bonded to the patient's teeth, and thereafter other appliances such as arch wires and force transmitting members are mounted on the brackets for applying corrective forces to the teeth.

The brackets are bonded to the teeth using adhesives after the teeth have been initially prepared for bonding. Tooth preparation might include applying a prophy paste on the tooth enamel surface, etching the areas of the tooth to be bonded with a conditioner, and sealing the etched surfaces with a sealant. After the teeth have been prepared, the brackets can be bonded to the teeth using a variety of bonding adhesives or cements such as "two mix" cements, "no mix", and light activated or light curable cements. Two mix cements require the clinician or orthodontist to mix two different pastes together to form an adhesive. Light curable cements can be activated or cured using a lamp after the brackets have been placed on the teeth. In accordance with one method of bracket bonding, these cements are prepared and applied to the base of the bracket immediately prior to placement of the bracket on the tooth.

Another method of bracket bonding (as described in U.S. Pat. No. 5,354,199 issued to Jacobs et al., U.S. Pat. 5,328,363 issued to Chester et al., U.S. Pat. No. 5,015,180 issued to Randklev and U.S. Pat. No. 4,204,325 issued to Kaelble) utilizes brackets that are precoated with a light activated cement. The cement is covered by releasable film and stored in a substantially light-proof container until use to inhibit premature activation of the cement. In U.S. Pat. No. 5,015,180, the orthodontic bracket includes a light curable paste sandwiched between the bracket base and a releasable cover sheet. To bond the bracket to a tooth, the cover sheet is removed from the paste, and the bracket base is applied to the tooth. A lamp is then used to transmit curing light to the bracket to cure the paste.

Such precoated brackets have been found to reduce chair time for the orthodontist because he or she need not spend time in preparing and dispensing adhesive paste or cement on the bracket base before applying the bracket to the tooth.

However, commercially available precoated brackets have a limited shelf life. If proper inventory rotation is not maintained by the clinician, the brackets can become overaged and unusable. In addition, the cost of the commercially available precoated brackets is high because the bracket manufacturer loses the cost efficiency associated with long production runs of one style of bracket in order to keep the inventory from becoming unusable due to overaging. These brackets are also expensive because they must be stored and sold in substantially light proof packaging, which typically includes a foil coating and individual packaging.

Moreover, the bracket packaging for limiting light exposure is bulky, making storage difficult, particularly in orthodontist offices that are crowded.

Furthermore, only a limited variety of precoated brackets are commercially available, which limits the choice of appliances available to the clinician.

Also, if the standard curvature of the bonding surface of a commercially available precoated bracket does not closely match the morphology of the tooth on which it is to be bonded, it may be difficult to properly bond the bracket on the tooth without performing the additional step of adding cement to the bracket.

SUMMARY OF THE INVENTION

In accordance with the invention, a bracket container is provided for storing a plurality of orthodontic brackets having bases coated with a light curable adhesive. The container includes a housing and a tray slidably mounted in the housing. The tray includes an upper surface having a plurality of recesses, each for receiving one of the brackets. The tray is movable between a closed position in which the housing covers the recesses in the upper surface of the tray and an open position in which at least some of the recesses of the tray are not covered by the housing. The housing comprises substantially opaque material to limit exposure of the brackets to light when the tray is in the closed position.

A method of bonding a set of orthodontic brackets to a patient's teeth is also provided. In accordance with the method, a set of orthodontic brackets suitable for bonding on the patient's teeth is first selected. Then, a light curable cement is applied on a rear bonding surface of the base of each bracket to prepare the bracket for bonding at a predetermined later time. Each bracket is placed in a tray that is inserted into a container to significantly limit exposure of the brackets to light. Next, the teeth of the patient are prepared for bonding. Each bracket is then retrieved from the container and placed on the tooth on which it is to be bonded. A curing light is then applied on the brackets to cure the cement on each bracket for bonding the bracket to the tooth.

DETAILED DESCRIPTION

Figure 1:
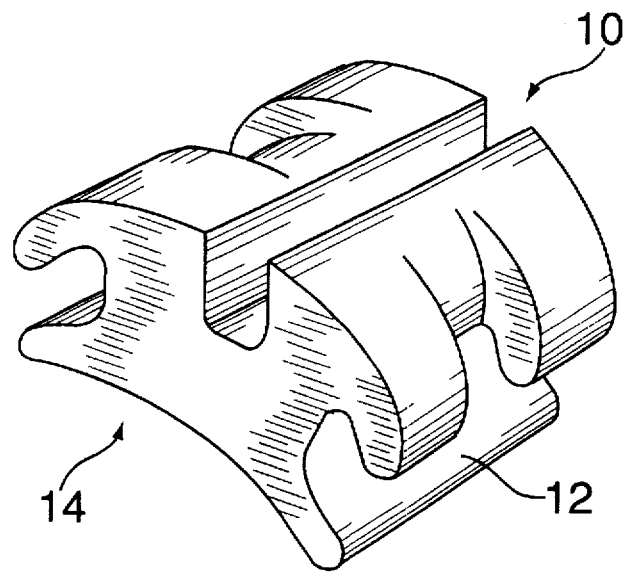
FIG. 1 is a perspective view of an exemplary orthodontic bracket.
Figure 4:
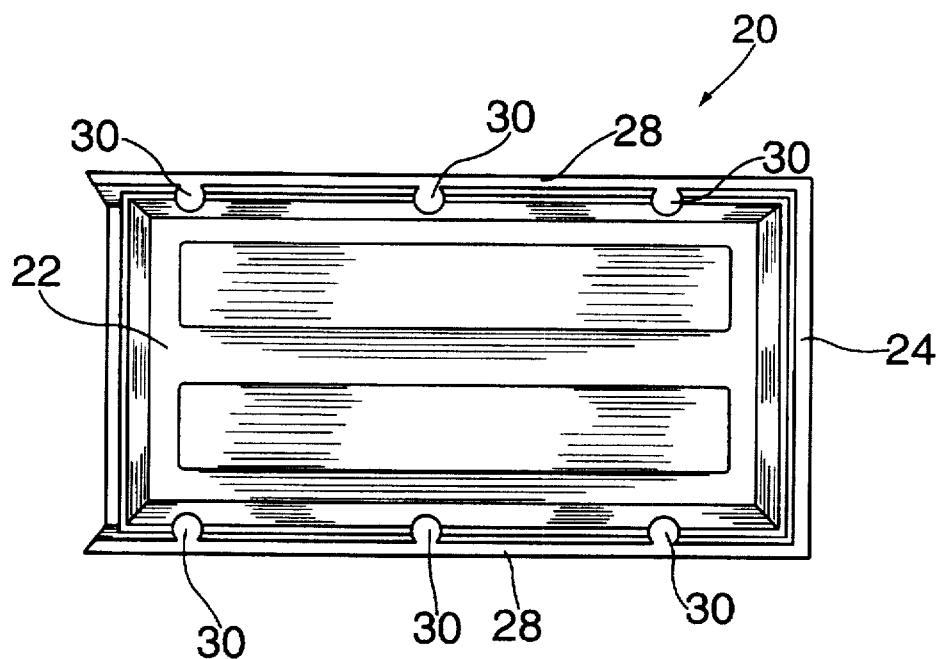
FIG. 4 is a bottom plan view of the container.
Figure 2:
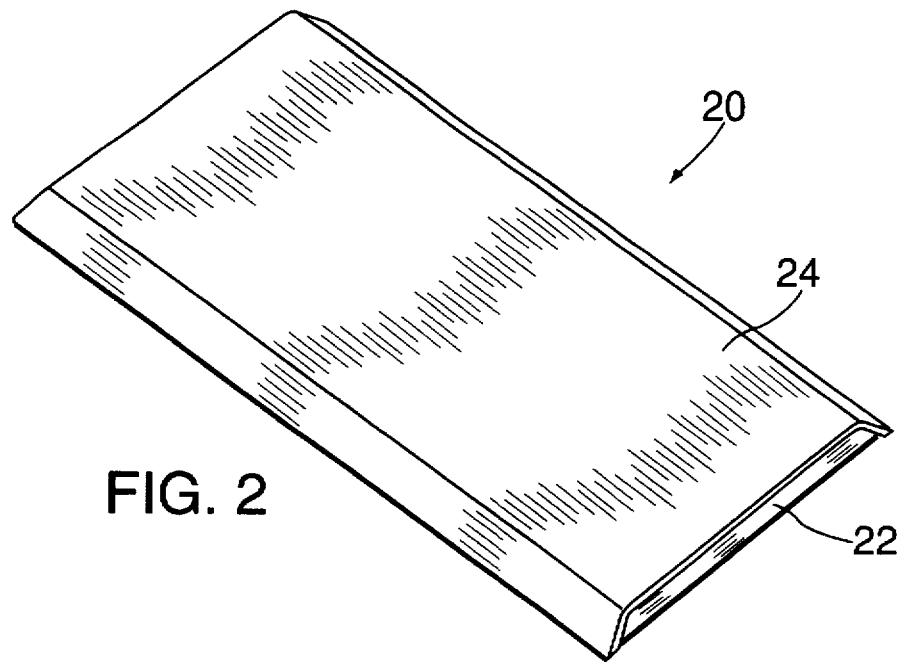
FIG. 2 is a perspective view of a container useable in a bracket bonding process in accordance with the invention, the container being in a closed position.
Figure 3:
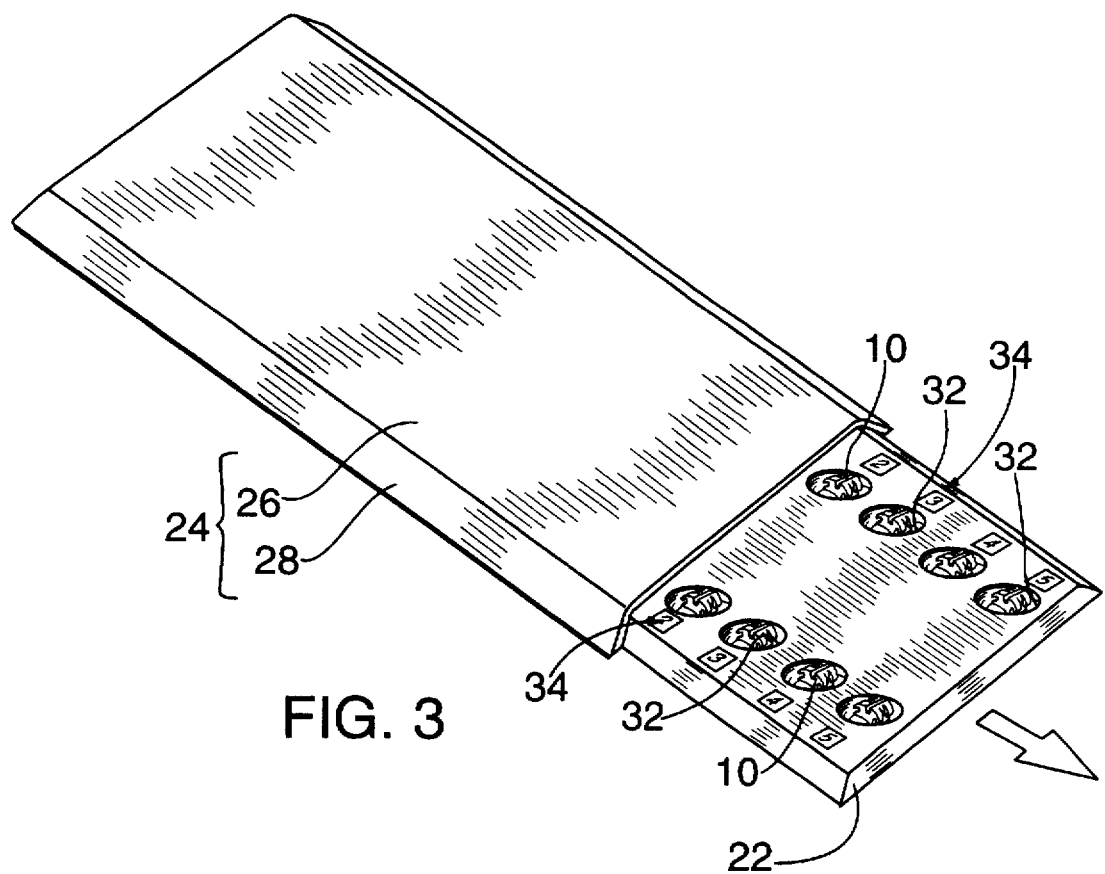
FIG. 3 is perspective view of the container in an open position.

FIG. 1 illustrates an example of one type of orthodontic bracket 10 used in orthodontic treatment. The bracket 10 includes a base 12 having a rear bonding surface 14 that can be bonded to the buccal surface of a tooth (not shown). FIGS. 2-4 illustrate a bracket container 20 for storing brackets prepared for bonding in accordance with the present invention. The container 20 comprises a tray 22 slidably mounted in a housing 24. The housing comprises a rectangular upper covering surface 26 and sidewalls 28 projecting from three sides thereof. The rear or underside of the housing 24 (shown in FIG. 4) includes a plurality of small projections 30 extending from the two opposing sidewalls 28 of the housing. The projections 30 support the underside of the tray 22 such that the tray 22 is slidably received in the housing 24.

The tray 22 includes a plurality of wells or recesses 32 on its upper surface, each for receiving a bracket 10 prepared for bonding as will be described further below. The recesses 32 are identified by markings or indicia 34 on the upper surface of the tray 22 adjacent each recess 32 to facilitate identification of the brackets 10 contained therein.

The housing 24 and the tray 22 comprise a substantially opaque plastic material having a sufficient thickness to act as a significant barrier to transmission of light therethrough. Also, the tray 22 is closely fitted in the housing 24. Accordingly, the container 20 substantially limits exposure of brackets 10 contained therein to light.

The bracket container 20 is used in an improved bracket bonding method in accordance with the invention. The method generally comprises preparing brackets 10 for bonding by applying a light curable cement on the bracket base 12, storing the brackets 10 in the bracket container 20, and, at some later predetermined time, retrieving the brackets 10 from the container 20 when needed for bonding on the patient's teeth.

More specifically, for example, in the morning prior to arrival of the patient at the clinician's office, the clinician consults the patient's records and selects a set of brackets to be used on the patient's teeth. The clinician is free to choose from a wide variety of commercially available appliances even those from different manufacturers to fit the patient's particular needs. For instance, the clinician may select Allure brand brackets on the maxillary central through the first bicuspid, standard edgewise brackets on the lower anteriors, and V-slot brackets on the lower cuspids and bicuspids. The clinician's dental assistant then applies a light curable cement to the base of each bracket. The brackets are then placed in the recesses of the tray, and the tray is slid into the housing to limit light exposure. The dental assistant then writes the patient's name on the bracket container with a grease pencil. When the patient arrives, his or her teeth are first prepared for bonding by the dental assistant. Thereafter, the orthodontist slides the tray out of the housing and retrieves each bracket. The brackets are placed on the teeth, and a lamp is used to cure the light curable cement on the brackets to bond the brackets on the teeth.

Should any of the brackets be found to be unusable due to severe tooth rotation or impaction, the cement on these brackets can be removed with an explorer, and the bracket can be reused on future patients.

As an example, the following steps might be taken to bond plastic brackets on a patient's teeth:

1. Dispense 2 or 3 drops of a primer into a dapper dish and cover the dish to limit its exposure to light.

2. Brush a thin layer of the primer to cover but not fill the rear bonding surface of the base of the bracket.

3. Wait 5 to 10 seconds and then apply a thin layer of a light curable cement on the bracket bonding surface while the primer is still wet.

4. Place the adhesive coated bracket in a recess of the tray designated for the tooth on which it is to be bonded. After all of the brackets needed for a patient have been placed in the tray, slide the tray into the housing to limit exposure of the brackets to light.

5. After the patient arrives at the clinician's office, prepare and prime his or her teeth as needed for the particular cement used on the brackets.

6. Pull the tray out of the housing, and place each bracket on a tooth, pushing it lingually against the tooth to seal it. Remove any excessive paste, which is also known as flash, from areas around the bracket base.

7. Light cure the cement for about 30 seconds by applying light from a lamp on the facial surface of the bracket to bond the bracket on the tooth.

As a further example, the following steps might be taken to bond metal or ceramic brackets to teeth:

1. Dispense 2 or 3 drops of a sealant resin into a dapper dish and cover the dish to limit its exposure to light.

2. Brush a thin layer of the sealant on the bonding surface of the bracket base without filling the base surface.

3. Apply a layer of light curable paste to the bracket bonding surface, and place the coated bracket into a recess in the tray designated for the tooth on which it is to be bonded. When all the brackets needed for the patient have been placed in the tray, slide the tray into the housing to limit exposure of the brackets to light.

4. After the patient arrives, prepare and prime his or her teeth as needed for the cement to be used.

5. Remove the brackets from the container and push the bracket bonding surface of each bracket lingually against a tooth surface. Remove any flash from areas around the bracket bases.

6. For metal brackets, light cure the adhesive for about 15 seconds from each of the incisal, gingival, mesial and distal surfaces of the brackets. For ceramic brackets, light cure the adhesive for 30 seconds from the labial or facial surface of each bracket.

One example of a light curable cement useable in the present bonding system is manufactured by MidWest Orthodontics Manufacturing of Columbus, Ind. The cement generally comprises silicon dioxide, methacrylate monomers and derivatives, and sodium fluoride. Other light activated cements such as those manufactured by Heliosit Orthodontics and sold by Ivoclar can also be used in the present bonding system. The primer may comprise methacrylate monomers and a photo initiator.

The present bonding system has been found to significantly reduce chair time for the clinician since he or she need not spend time in preparing and applying cement on the brackets before bonding the brackets to the teeth. In addition, the present bonding system does not suffer from many of the drawbacks of commercially available precoated brackets. For instance, the clinician is free to choose substantially any commercially available uncoated bracket to meet a particular patient's needs. Also, these buckets are less costly since they are not precoated by the manufacturer. Furthermore, the brackets need not be purchased and stored in expensive and bulky packaging for limiting light exposure. Moreover, the clinician need not be concerned with maintaining inventory control to avoid bracket averaging since cement is applied to the brackets when needed.

It is claimed:

1. A bracket container for storing a plurality of orthodontic brackets having bases coated with a light curable adhesive, said container comprising:

a housing comprising an upper covering surface and three sidewalls extending downwardly from three sides of the covering surface, said housing further comprising projections extending from said sidewalls; and a tray slidably mounted in said housing and supported by said projections, said tray including an upper surface having a plurality of recesses, each for receiving one of said brackets, said upper surface of said tray also including markings thereon for identifying said recesses or the brackets contained therein, wherein said tray is movable between a closed position in which said upper covering surface of said housing covers said recesses and an open position in which at least some of said recesses are not covered by said housing, said housing comprising substantially opaque material to limit exposure of said brackets to light when said tray is in the closed position.

2. The bracket container of claim 1, wherein said housing and tray each comprise molded plastic.

3. A method of bonding a set of orthodontic brackets to a patient's teeth, comprising the steps of:

(a) selecting a set of orthodontic brackets suitable for bonding on said patient's teeth;

(b) applying a light curable cement on a rear bonding surface of the base of each bracket to prepare the bracket for bonding at a predetermined later time;

(c) placing each bracket in a tray of a container, said tray being slidably mounted in a housing, and inserting the tray into the container housing to significantly limit exposure of the brackets to light;

(d) preparing the teeth for bonding;

(e) retrieving the brackets from the tray in the container at the predetermined later time, and placing each bracket on the tooth on which it is to be bonded; and (f) applying a curing light on said brackets to cure the cement on each bracket for bonding the bracket to the tooth.

4. The method of claim 3, wherein said tray includes an upper surface having a plurality of recesses, each for receiving one of said brackets, wherein said tray is movable between a closed position in which said housing covers said recesses in said upper surface of the tray and an open position in which at least some of said recesses of said tray are not covered by said housing, said housing comprising substantially opaque material to limit exposure of said brackets to light when said tray is in the closed position.

5. The method of claim 3, further comprising the step of brushing a thin layer of primer on the rear bonding surface of the base of each bracket before step (b).

6. The method of claim 3, further comprising the step of brushing a layer of sealant on the rear bonding surface of the base of each bracket before step (b).

7. The method of claim 3, further comprising the step of removing any flash from areas around the bracket base after step (e).

* * * * *